United States Patent [19]

Nonomura

[11] Patent Number: 5,555,884
[45] Date of Patent: Sep. 17, 1996

[54] MEASURING METHOD BY USING RESONANCE OF A RESONANCE MEDIUM

[75] Inventor: Yuusuke Nonomura, Nagoya, Japan

[73] Assignee: Kabushiki Kaisha Egawa, Nagoya, Japan

[21] Appl. No.: 160,162

[22] Filed: Dec. 2, 1993

[30] Foreign Application Priority Data

Dec. 16, 1992 [JP] Japan .................................. 4-336089
Jan. 19, 1993 [JP] Japan .................................. 5-006816
Feb. 18, 1993 [JP] Japan .................................. 5-029474

[51] Int. Cl.$^6$ .................................................. A61B 5/055
[52] U.S. Cl. .................................. 128/653.2; 128/653.4; 433/223; 623/901
[58] Field of Search ........................... 128/653.2, 653.4, 128/653.5; 433/223; 623/901

[56] References Cited

U.S. PATENT DOCUMENTS

| | | | |
|---|---|---|---|
| 4,575,805 | 3/1986 | Moermann et al. | 433/223 |
| 5,221,204 | 6/1993 | Kruger et al. | 433/173 |
| 5,266,030 | 11/1993 | Van Der Zel | 433/223 |
| 5,268,165 | 12/1993 | Hedlund et al. | 128/653.4 |

FOREIGN PATENT DOCUMENTS 2-218348  8/1990  Japan .

*Primary Examiner*—Ruth S. Smith
*Attorney, Agent, or Firm*—Sughrue, Mion, Zinn, Macpeak & Seas

[57] ABSTRACT

The present invention relates to a method and an apparatus for determining the shape of a tooth, a prosthesis, a jaw bone, or an implant structure with an Magnetic Resonance Imaging device. However, since these items lack a substantial number of protons, electrons, or molecules which can be detected by an Magnetic Resonance Imaging device, these items are supplied with an Magnetic Resonance Imaging contrast medium which is rich in such protons, electrons, or molecules. Therefore, once the Magnetic Resonance Imaging contrast medium is supplied to the tooth, prosthesis, jaw bone, or implant structure, the Magnetic Resonance Imaging device can measure the items by measuring the Magnetic Resonance Imaging contrast medium surrounding the items. Furthermore, an electrical circuit may be provided which can determine the shape of the tooth, prothesis, jaw bone, or implant structure based on the measurements of the Magnetic Resonance Imaging device. Also, a three dimensional cutter may be provided which can create a crown or other implant based on the shape determined by the electrical circuit.

16 Claims, 12 Drawing Sheets

MEASURING METHOD BY USING RESONANCE OF A RESONANCE MEDIUM

BACKGROUND OF THE INVENTION

1. Field of the Invention

This invention relates to a method of measuring a figure, positioning and displacement of articles by artificially applying electrical, magnetic and electromagnetic fields. Furthermore, the present invention is well-suited for a dental therapy, but not limited to the dental therapy.

2. Description of Prior Art

As a method of magnetically measuring a sectioned shape of a living body by using a resonance medium in the living body, a MRI device has been introduced. In the MRI device, a magnetic field is applied to the living body to control the spinning direction of hydrogen protons so as measure the sectional figure of the living body on the basis of the spin state (resonance state) by using a resonance medium (such as mobile hydrogen protons, hydrogen nucleus mainly in $H_2O$) in the living body. Because the MRI device utilizes the hydrogen protons in the living body as a resonance medium, it is not possible to precisely measure articles which lacks or is short of mobile hydrogen protons. As one example of the articles, it is not possible to precisely measure the shape of teeth and figures of the lost portion of teeth at the time of dental therapy because of the shortage of the mobile hydrogen protons.

In the MRI device which utilizes the resonance of the living body, it is not possible to measure a displacement (rotational and linear) of changing portions in non-living body. However, a potential meter has been known to measure a displacement (rotational and linear) of changing portions in non-living body. In this potential meter, a resistance changes according to the changed position of the articles, and the rotational and linear displacements are measured on the basis of the voltage change due to the increase or decrease of the resistance. In this case, the potential meter is electrically connected to a voltage measurement device via a lead wire. It is suggested that the voltage value measured by the potential meter is transformed into signals which is measured by non-contact technique. However, a peripheral device of the potential meter requires a large scaled architecture and a complicated and heavy weight structure.

Therefore, it is a first object of the invention to provide a method of measuring article which is capable of precisely measuring a figure by applying a resonance medium due to the spinning action of the protons.

It is a second object of the invention to provide a method of measuring an article which is capable of precisely measuring a figure by applying a resonance medium due to the electronic spin.

It is a third object of the invention to provide a method of measuring an article which is capable of precisely measuring a figure through non-contact by applying a resonance medium due to the electronic device. Namely, it is an object of the invention to provide a method of measuring shape, position and displacement of the article by using the resonance of the resonance medium (protons, electrons, molecule and combination of these matters).

SUMMARY OF THE INVENTION

According to the invention, there are provided articles in a mouth such as teeth, prosthesis, jaw bone, and an implant structure which lack or is short or mobile hydrogen protons. These articles are covered by a MRI contrast medium which contains a lot of mobile hydrogen protons, and measured by a MRI device through the contrast medium. That is to say, these articles are measured via the contact surface of the contrast medium. This enables one to measure the shape of the articles such as teeth, prosthesis, a jaw bone, and an implant structure which lack or are short of mobile hydrogen protons.

According to the invention, there are provided articles such as teeth, prosthesis, a jaw bone, and an implant structure which lack or are short of mobile hydrogen protons. These articles are covered by contrast medium which contains a lot of mobile hydrogen protons, and measured by using a resonance of the resonance medium. This makes it possible to measure the articles such as teeth, prosthesis, a jaw bone, and an implant structure which lack or are short of mobile hydrogen protons by means of the MRI device through the MRI contrast medium.

According to a preferred embodiment of the invention, the articles to be measured are prepared teeth. The prepared teeth are supplied with the MRI contrast medium, and shapes of the prepared teeth are measured by MRI device. This enables one to precisely measured the shapes of the teeth without using an impression method of the prior art.

According further to the invention, the prepared teeth are supplied by the contrast medium which contains a lot of mobile hydrogen protons, and measured by the MRI device. On the basis of the measured shape of the tooth, a shape of a prosthetic filler is determined which is applied to the tooth. On the basis of the determined shape of the prosthetic filler, the prosthetic filler three-dimensionally cut to provide the prosthetic filler.

According further to the invention, a device for making a crowning prosthetic filler comprises: an MRI device which measures a shape of tooth which is supplied with a contrast medium rich in mobile hydrogen protons; an electrical circuit which measures the shape of the tooth by the MRI device through the contrast medium so as to determine the shape of the crowning prosthetic filler; a three-dimensional cutter which provides the crowning prosthetic filler on the basis of the shape determined by the electrical circuit. Also a measurement method is provided to measure the article by using the resonance of the resonance medium.

According still further to the invention, the crowning prosthetic filler is directly created according to the shape of the tooth obtained from the MRI device. This enables one to precisely and quickly manufacture the crowning prosthetic filler as compared to the prior art in which the impression method is used.

According further to the invention, the article to be measured is provided a root of the tooth in which a dental pulp is removed. The root of the tooth is supplied with a contrast medium rich in mobile hydrogen protons, and measured by the MRI device. On the basis of the data from the MRI device, a shape of the dental root is measured to determine a specific shape of a prosthetic filler which is supplied to the dental root. From the determined shape of the dental root, the prosthetic filler is created by means of a three-dimensional cutter.

According further to the invention, the prosthetic filler is directly created according to the shape of the dental root obtained from the MRI device. This makes it possible to provide a long-lasting and stable prosthetic filler as compared to the prior art in which a synthetic resin is supplied to the dental root.

According to the invention, there are provided articles such as teeth, prosthesis, a jaw bone, and an implant structure which lack or are short of mobile hydrogen protons. These articles are supplied with a contrast medium which contains a lot of magnetic material, and measured by a MRI device through the contrast medium. This enables one to provide a measurement method to measure the articles by using the resonance of the resonance medium.

According to the invention, there are provided articles such as teeth, prosthesis, a jaw bone, and an implant structure which lack or are short of mobile hydrogen protons. These articles are supplied by a contrast medium fluid which contains a lot of magnetic material, and measured by a MRI device through the contrast medium by using the resonance of the resonance medium.

According further to the invention, the article to be measured is a root of the tooth in which a dental pulp is removed. The root of the tooth is supplied with a contrast medium rich in material, and measured by the MRI device. On the basis of the data from the MRI device, a shape of the dental root is measured to determine a shape of a prosthetic filler which coats to the dental root. From the determined shape of the dental root, the prosthetic filler is created by means of a three-dimensional cutter. This enables one to directly create the prosthetic filler according to the shape of the dental root obtained from the MRI device. This makes it possible to provide a long-lasting and stable prosthetic filler as compared to the prior art in which a synthetic resin is coated to the dental root.

According further to the invention, an insert probe is inserted in the living body, and measured by the MRI device. This enables one to provide a measuring method by using the resonance of the resonance medium in which the position of the insert probe is determined.

According further to the invention, the position of the insert probe is measure by the MRI device. This enables to significantly improve the dental treatment technique.

According further to the invention, a measuring method which uses the resonance of the resonance medium comprises: providing a resonance circuit which changes a frequency according to displacement of the articles and providing a resonance frequency measuring device to measure the position of the article on the basis of the resonance frequency obtained from the resonance frequency measuring device. This enables one to measure the displacement of the article by non-contact means on the basis of the resonance frequency of the resonance medium. The resonance circuit is realized with a small scaled architect and light weight structure.

According further to the invention, a measuring method which uses the resonance of the resonance medium comprises: providing a resonance circuit which changes a frequency according to displacement of the articles; providing a resonance frequency measuring device; providing a calculator device which calculates the position of the article on the basis of the resonance frequency obtained from the resonance frequency measuring device.

According further to the invention, a measurement device makes it possible to detect a displacement of the article by the resonance frequency of the resonance medium.

These and other objects and advantages of the invention will be apparent upon reference to the following specification, attendant claims and drawings.

DETAILED DESCRIPTION OF PREFERRED EMBODIMENTS OF THE INVENTION

Figure 1:
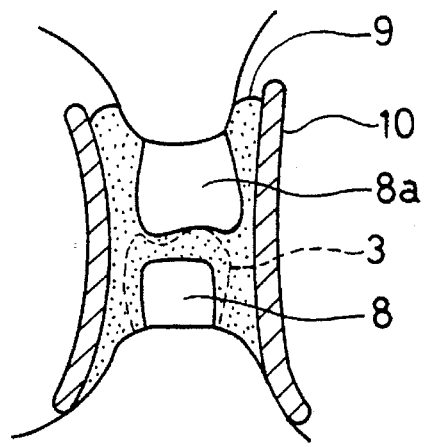
FIG. 1 is a plan view for explaining a MRI contrast medium retained to a measuring cover according to a first embodiment of the invention.
Figure 2:
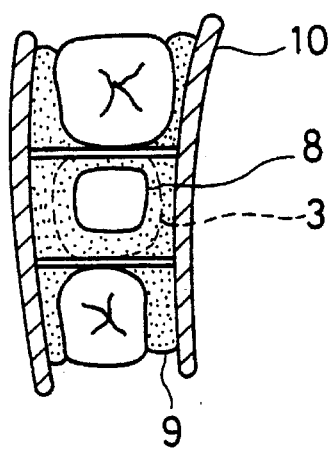
FIG. 2 is an upper plan view for explaining a MRI contrast medium retained to a measuring cover according to the first embodiment of the invention.
Figure 3:
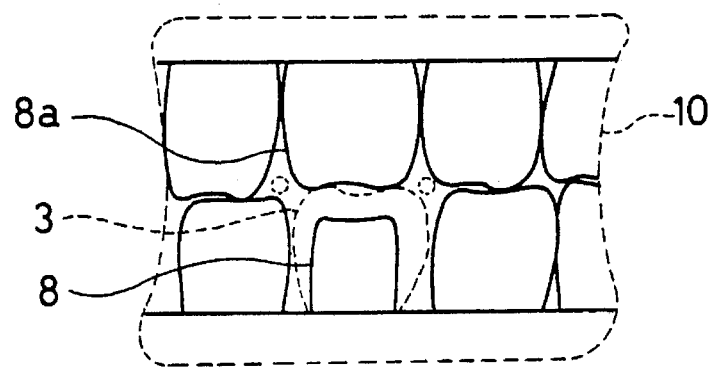
FIG. 3 is a side elevational view of a cure tooth according to the first embodiment of the invention.
Figure 4:
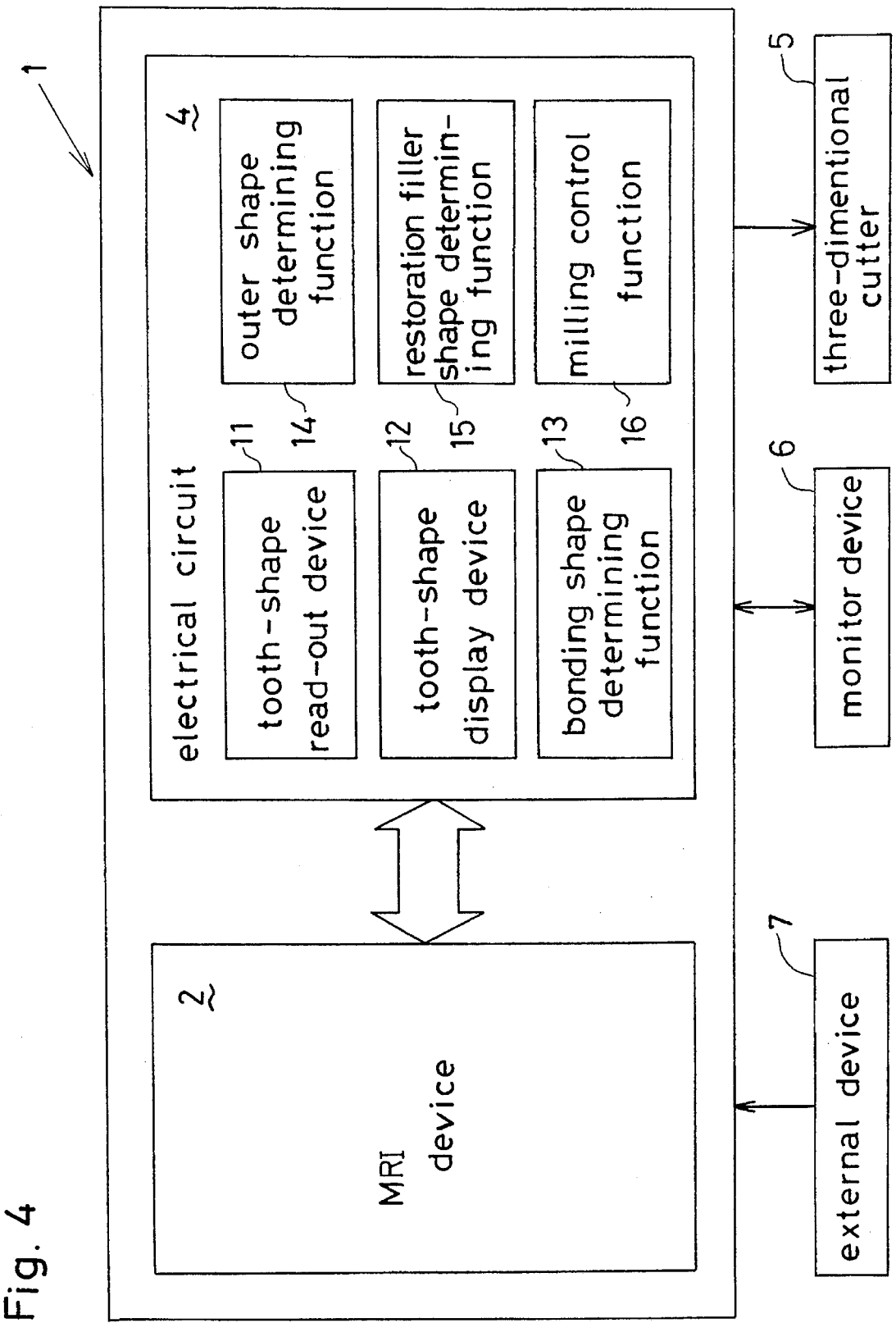
FIG. 4 is a schematic block diagram of a prosthetic filler according to the first embodiment of the invention.

Referring to FIG. 1, which shows a cure tooth 8 which is short of hydrogen protons, the cure tooth 8 is supplied with a MRI prosthetic filler 9 according to a first embodiment of the invention. In this instance, the tooth 8 is supplied with the MRI prosthetic filler 9, but the thickness of the coating is freely selected as required. The shape of the cure tooth 8 is measured by a MRI device 2. FIG. 4 illustrates an example of a schematic block diagram of a restoration device 1 which makes a tooth restoration filler 3. The restoration device 1 has a MRI device 2 and an electrical circuit 4 which determines the shape of the tooth restoration filler 3 (see FIGS. 1–3) on the basis of the information from the dental shape obtained by the MRI device 2. A three-dimensional cutter 5 is adapted to define the shape of the tooth restoration filler 3. The MRI device 2 is a well-known structure, and has a magnetic field generator device and a magnetic resonance reading device which reads the spin state or electronic spin state of hydrogen protons. A shape measuring device is provided to detect the presence of the hydrogen protons from the magnetic resonance read out by the magnetic resonance reading device and calculates a shape in which the hydrogen protons are present. The calculated shape is monitored by an external display device 6. The MRI device 2 is operated by an operator through the electrical circuit 4 and an external device 7. In the MRI device 2, the cure tooth 8 is supplied with the MRI prosthetic filler 9, and the shape of the MRI prosthetic filler 9 is measured to determine the shape of the cure tooth 8. The MRI prosthetic filler 9 fills between the cure tooth 8 and a measurement cover device 10 which is applied to the outer surface of the cure tooth 8 as shown in FIGS. 1 through 3. The measurement cover device 10 is provided to support the MRI prosthetic filler 9 at both sides of the cure tooth 8 at the time of measuring the shape of the cure tooth 8. In this instance, care should be taken not to interfere the occlusion of the teeth (particularly when examining occlusive positions such as central occlusion, eccentric occlusion and the like) in which a tooth 8a occludes the tooth restoration filler 3 which is applied to the cure tooth 8. When the shape of the cure tooth 8 and the occlusive position are measured by the MRI device 2, the cure tooth 8 is covered by the measurement cover device 10. Then the MRI prosthetic filler 9 is supplied inside the measurement cover device 10 so as to completely coat an outer surface of the cure tooth 8. The MRI prosthetic filler 9 includes inorganic and organic substance such as agar, alginate, silicon rubber, and hydrocarbon which are rich in mobile hydrogen protons (mainly in $H_2O$). The MRI prosthetic filler 9 is in a liquid (or semi solid) state at least when placed in the mouth to coat the cure tooth 8. The MRI prosthetic filler 9 performs better when it is not solidified in the mouth (particularly upon measuring the consecutive occlusive positions of the teeth). When the MRI contrast medium is solidified in the mouth, the solidified MRI contrast medium collapses upon changing the occlusive position of the teeth. When consecutively changing the occlusive position of the teeth, the MRI prosthetic filler 9 may be constantly supplied inside the measurement cover device 10 so as to avoid the clearance around the cure tooth 8 by using a syringe, for example. When it is necessary to prevent measurement errors due to the displacement of the patient's jaw, the MRI contrast medium may be liquid when the contrast medium is in the mouth to coat the cure tooth 8, and the contrast medium may preferably be solidified after coating the cure tooth 8. When the cure tooth 8 is supplied with the MRI prosthetic filler 9, the cure tooth 8 is prepared, and the prosthetic filler 9 is measured by the MRI device 2. The shape of the prepared cure tooth 8 is determined by the shape of the prosthetic filler 9 which is in direct contact with the cure tooth 8. It is noted that in the above description, the inner shape of the MRI contrast medium 9 is measured while the cure tooth 8 is covered by the MRI contrast medium 9. However, the MRI contrast medium 9 may be solidified in the mouth, and the solidified medium 9 may be taken out of the mouth to be measured by the MRI device 2. Also, the MRI contrast medium 9 may be taken out of the mouth and may be supplied with a discrete MRI contrast medium. Then, the interface between the two MRI contrast media can be measured by the MRI device 2 so as to determine the shape of the cure tooth 8. In this instance, a discrete medium may be provided in an inner side of the contrast medium 9 when the contrast medium 9 is separated from the cure tooth so as to indirectly measure the shape of the cure tooth 8 by way of the newly produced medium. Thus, measuring the MRI contrast medium 9 outside the mouth makes it possible to avoid from directly applying the MRI device 2 to the patient, and thus eliminating the inconvenience of directly applying the MRI device 2 to the patient. When the discrete contrast medium is supplied to the MRI contrast medium 9 outside the mouth, it is possible to use a discrete contrast medium which is inappropriate for the mouth.

In the electrical circuit 4, the electrical circuit 4 has a tooth shape read-out device 11 which reads the shape of the tooth from the spin state of the protons in the MRI prosthetic filler 9. A tooth shape display device 12 is provided to display the shape of the tooth read out by the tooth shape read-out device 11 through a monitor device 6. By observing the shape of the tooth on the monitor device 6, the external device 7 is operated to specify a bonding shape which matches to the cure tooth 8 by a bonding shape determining function 13. By considering the occlusive position of the teeth, the shape of the MRI prosthetic filler 9 is simulated by the operation of the external device 7 by an outer shape determining function 14. From the bonding shape specified by the bonding shape determining function 13 and the outer shape determined by the outer shape determining function 14, the shape of the MRI prosthetic filler 9 is determined by a restoration filler shape determining function 15.

The electrical circuit 4 has a milling control function 16 which controls the three-dimensional cutter 5 to provide the MRI prosthetic filler 9 with the outer shape specified by the restoration filler shape determining function 15. The milling control function 16 and the three-dimensional cutter 5 can create the tooth restoration filler 3 from various type of metals, ceramic material and the like.

According to the first embodiment of the invention, the shape of the MRI prosthetic filler 9 is precisely measured by coating the cure tooth 8 with the MRI prosthetic filler 9 despite the fact that it is difficult to directly measure the cure tooth 8 by the MRI device 2. From the shape of the MRI prosthetic filler 9 which is in contact with the cure tooth 8, the shape of the cure tooth 8 and various types of the occlusive positions between the cure tooth 8 and the tooth 8a are precisely measured. From the prepared shape of the cure tooth 8 and information of the occlusive positions, the shape of the tooth restoration filler 3 is determined. Then, the tooth restoration filler 3 can be manufactured by CAD (computer-aided machine). The restoration device 1 enables one to make the tooth restoration filler 3 on the basis of the precisely measured tooth shape without using the impression method. This makes it possible to precisely and quickly manufacture the tooth restoration filler 3 compared to the prior art in which the impression is used in the patient mouth.

Figure 5:
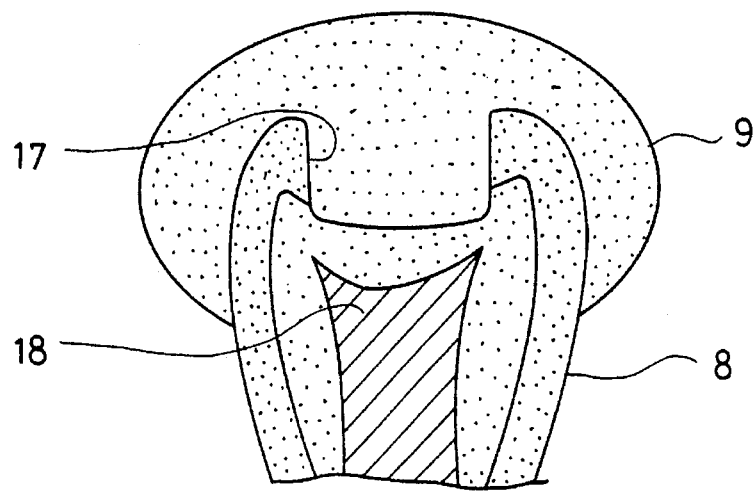
FIG. 5 is a cross sectional view of a cavity of the tooth in which the MRI contrast medium is provided according to a second embodiment of the invention.

FIG. 5 show a cross sectional view of the tooth 8 which has a cavity 17 provided on the tooth 8 at the time of curing the tooth 8 according to a second embodiment of the invention. The cavity 17 is filled with the MRI prosthetic filler 9, and the shape of the cavity 17 is measured by using the MRI device 2. It is appreciated that the tooth restoration filler 3 is precisely and quickly manufactured on the basis of the shape of the cavity 17 by using the restoration device 1. A distance between the cavity 17 and a dental pulp 18 of the cure tooth 8 is measured by filling the cavity 17 with the MRI prosthetic filler 9 and using the MRI device 2 because the dental pulp 18 is rich in mobile hydrogen protons. In the prior art in which the preparing amount of the cavity 17 and the distance between the cavity 17 and the dental pulp 18 of the cure tooth 8 are not measured, the dental pulp is often prepared inadvertently. According to the invention, the preparing amount of the cavity 17 and the distance between an inner wall of the cavity 17 and the dental pulp 18 of the cure tooth 8 are measured respectively. This apparently makes it possible to prevent the dental pulp from being prepared inadvertently.

Figure 6:
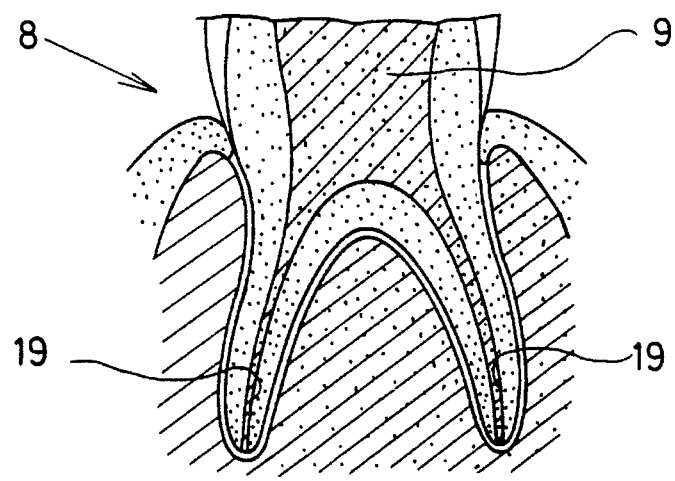
FIG. 6 is a cross sectional view of a root of the tooth in which the MRI contrast medium is provided according to a third embodiment of the invention.

FIG. 6 shows a cross sectional view of the cure tooth 8 in which the dental pulp in a pulp root canal 19 is removed by a reamer, a file, or the like. Within the pulp root canal 19 in which the dental pulp is removed, the MRI prosthetic filler 9 is filled, and the shape of the pulp root canal 19 is measured by using the well-known MRI device 2. By using the restoration device 1, tooth restoration filler 19a which fills the pulp root canal 19 is precisely and quickly made on the basis of the measured figure of the pulp root canal 19.

In the prior art in which a synthetic resin is provided with dental root from which the dental pulp is removed, tissue change and dead voids often appear in the tooth to which finally results in inflammation. With the use of the MRI prosthetic filler 9 in combination with the MRI device 2, it is possible to cure the dental root without any tissue change and dead voids in the tooth so as to prevent occurrence of the inflammation.

Figure 8:
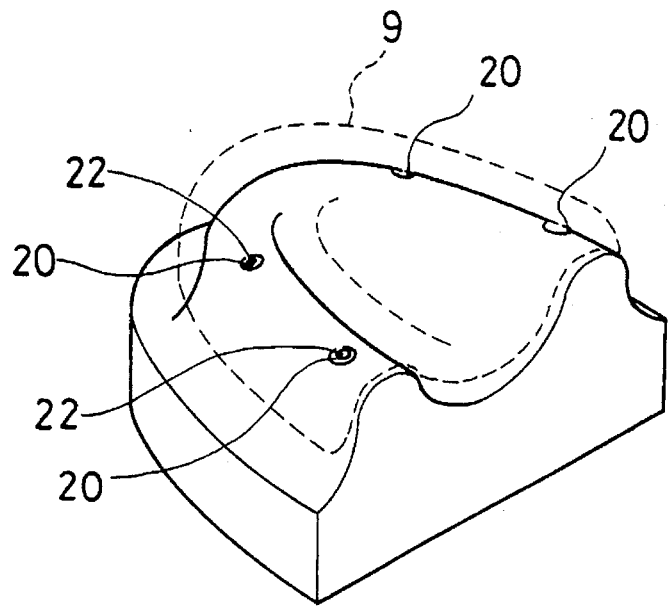
FIG. 8 is a schematic perspective view of an implant structure according to a fourth embodiment of the invention.
Figure 9:
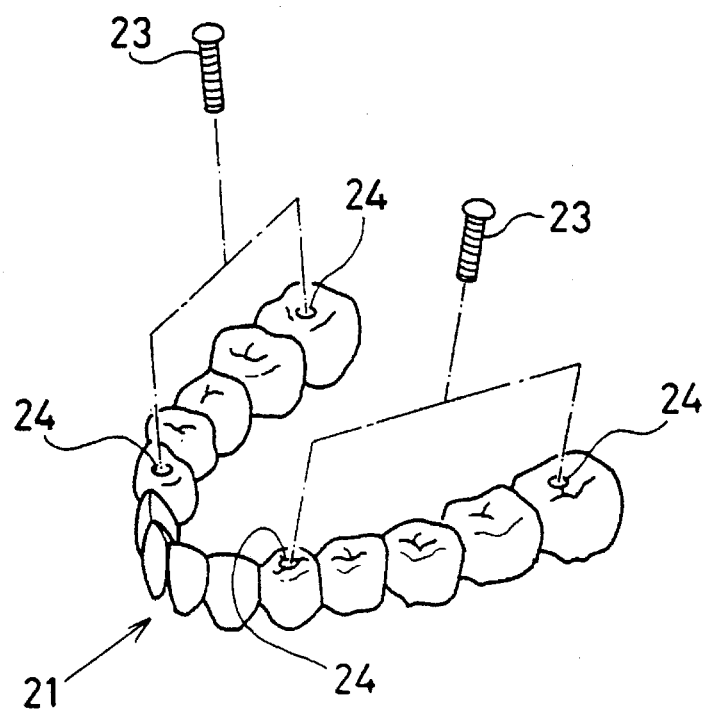
FIG. 9 is a schematic perspective view of a prosthesis which is to be bonded to the implant structure according to the fourth embodiment of the invention.

FIG. 8 shows an implant structure 20 which is attached to a jaw bone and which serves as an article to be measured according to an eighth embodiment of the invention. The implant structure 20 is supplied by the MRI prosthetic filler 9. By measuring the prosthetic filler 9 with the MRI device 2, the position and the direction of a screw hole 22 are determined in order to correctly attach a prosthesis 21 to the implant structure 20. On the basis of the position and the direction of the screw hole 22, a throughhole 24 in which a screw 23 passes is formed on the prosthesis 21 by using the three-dimensional cutter such as CAD (computer-aided machine) as shown in FIG. 9.

Figure 10:
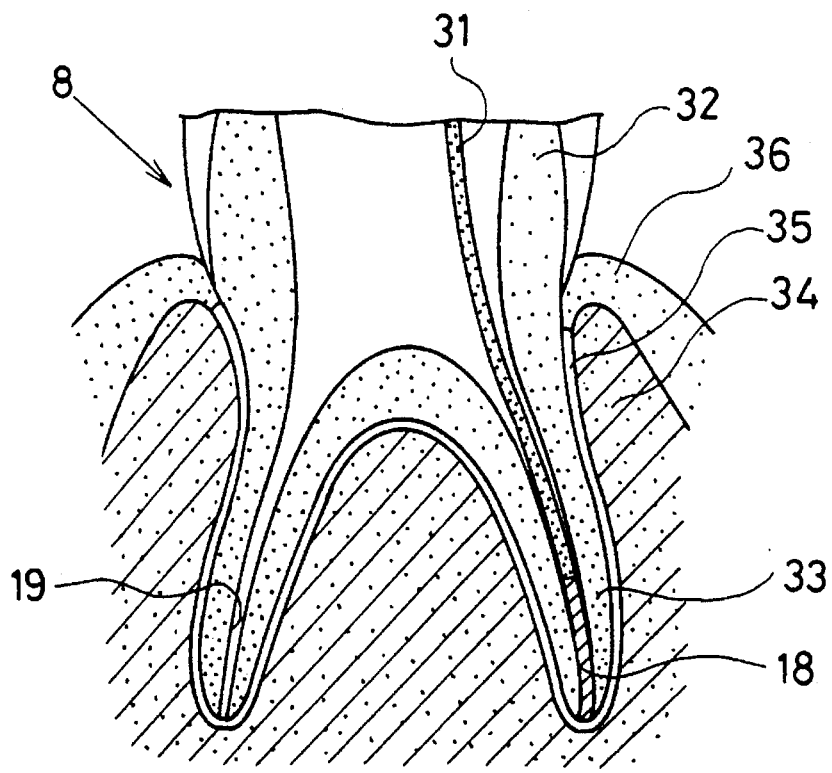
FIG. 10 is a cross sectional view of the prosthesis in which a dental pulp is removed according to a fifth embodiment of the invention.
Figure 11:
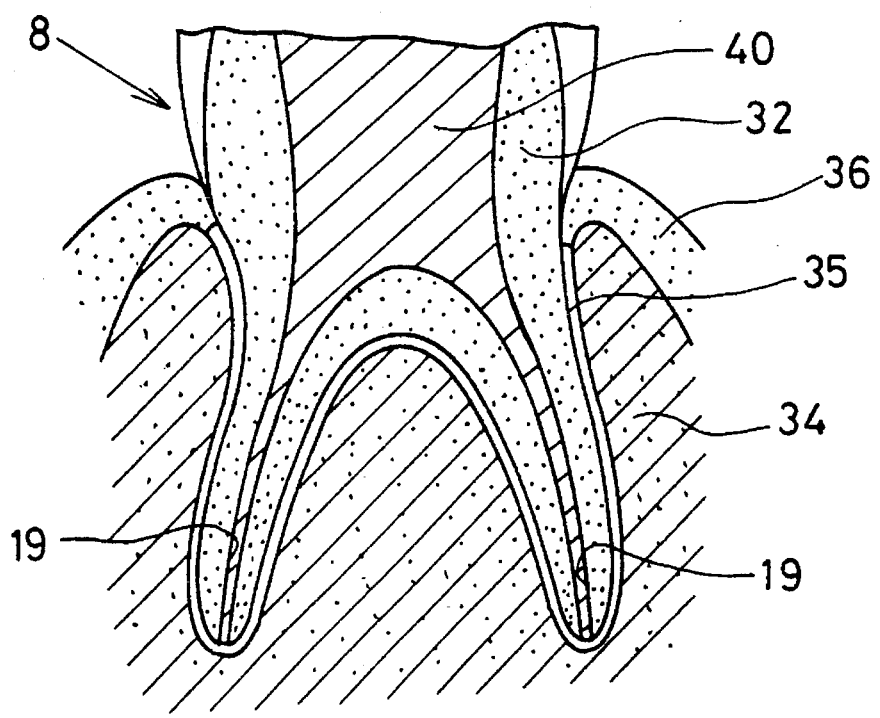
FIG. 11 is a cross sectional view of the tooth in which a prosthetic filler is coated to the dental root according to the fifth embodiment of the invention.

FIG. 10 shows the cure tooth 8 in which a preparing probe (insert probe) 31 is inserted to remove the dental pulp 18 inside the pulp root canal 19. As one example of curing the pulp root canal 19, the dental pulp is exposed by preparing the cure tooth 8. Then the preparing probe 31 such as a reamer, a file, or the like is inserted in the dental pulp 18. In this instance, the preparing probe 31 is made of flexible and magnetic metal or oxide of such as Fe, Co, Cu, Ni, Cr, Mn, Sr, Sm and Nd or alloy of these magnetic metals such as a stainless steel. Upon inserting the preparing probe 31 in the dental pulp 18, the MRI device 2 is operated to show the cure tooth 8 (pulp root canal 19 in particular) or a section of the pulp root canal 19 by means of the three-dimensional structure. The hard portions 32 such as dentin and enamel of the cure tooth 8 can not be measured by the MRI device 2. However, the preparing probe 31 is measured by the MRI device 2 because of the electronic spin. A gum 36, the dental pulp 18, the dental root 33 and a dental root membrane 35 between the dental root 33, and alveolus bone 34 are measured by the MRI device 2 to clearly show the preparing probe 31, the gum 36, the dental pulp 18 and the dental root membrane 35 on the monitor device 6.

By confirming the amount of insertion of the insert probe 31, the operator places a leading end of the insert probe 31 on the dental root base. Then the operator manipulates a stopper (not shown) not to proceed the leading end of the insert probe 31 inside the cure tooth 8. After the end of this manipulation, the dental pulp 18 is removed by the insert probe 31. The operator can initiate the cure of the cure tooth 8 after confirming that the insert probe 31 reaches the dental root base, and that the leading end of the insert probe 31 is not beyond the pulp root canal 19 of the cure tooth 8. This makes it possible to readily remove the dental pulp 18 without letting the probe 31 go beyond the pulp root canal 19 and without leaving any of the dental pulp 18 inside the cure tooth 8.

In this embodiment of the invention, the amount of insertion of the preparing probe 31 is first measured to remove the dental pulp 18. Upon removing the dental pulp 18, the cure tooth 8 (pulp root canal 19 in particular) is shown on the monitor device 6 by operating the MRI device 2, and then the dental pulp 18 may be removed from the end base of the pulp root canal 19 while simultaneously confirming the amount of insertion of the preparing probe 31 as indicated in FIG. 10. This also makes it possible to readily remove the dental pulp 18 without letting the probe 31 go beyond the pulp root canal 19 and without leaving any of the dental pulp 18 inside the cure tooth 8. This further makes it possible to effectively prevent the preparing probe 31 from pushing the dental pulp 18 out of the pulp root canal 19. In measuring an inside shape of the pulp root canal 19 from which the dental pulp 18 is removed, the inside of the pulp root canal 19 is filled with a liquid (or semi solid) MRI contrast medium 40 which is rich in magnetic material by using the syringe, lentulo or the like. A MRI contrast medium 40 is in the liquid state at least when the outer surface of the pulp root canal 19 is supplied with the MRI contrast medium 40. After coating the pulp root canal 19, the MRI contrast medium 40 may be solidified without keeping the fluidity. It is preferable that the MRI contrast medium 40 may be readily removed after measuring it by using the MRI device 2. By way of illustration, the MRI contrast medium 40 may be made by dispersing the magnetic material into water-soluble substance such as agar, otherwise dispersing it into the gum-like resin.

As examples of the magnetic materials, oxides or the metals of Fe, Co, Ni, Cu, Cr, Mn, Sr, Sm, and Nd are used in the powdered or ionized (chelated) form. In the case of the minutely powdered form, Samarium, Cobalt, Ferrite, Alnico, Permalloy, Sendust (trademark) and Fe—Si—B and Nd—Fe—B may be used as the magnetic materials.

Figure 7:
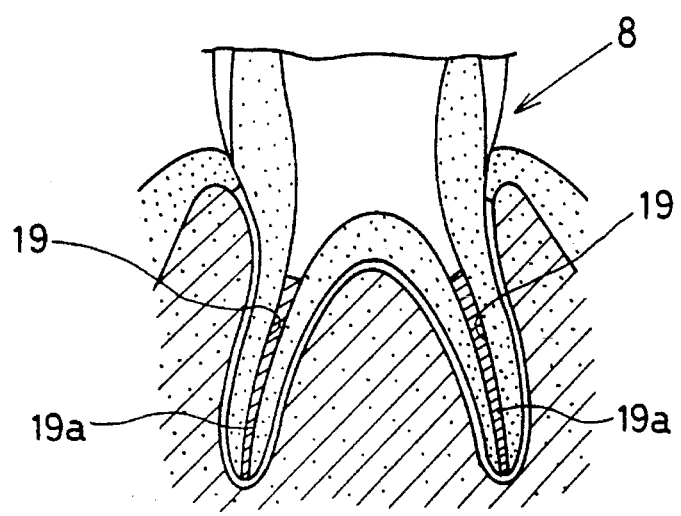
FIG. 7 is a cross sectional view of a root of the tooth in which the prosthetic filler is provided according to the third embodiment of the invention.

When the MRI device 2 examines the cure tooth 8 in which the pulp root canal 19 is supplied with the MRI contrast medium 40, the shape of the pulp root canal 19 is clearly shown due to the electronic spin in the MRI contrast medium 40. The electrical circuit 4 has the same structure as described in the first embodiment of the invention. Namely, the electrical circuit 4 includes the tooth shape read-out device 11 which reads the inner shape of the contrast medium 40 which is in direct contact with the cure tooth 8 on the basis of the shape of the MRI contrast medium 40 obtained by the MRI device 2. The tooth shape display device 12 displays the shape of the tooth read out on the monitor device 6 by the tooth shape read-out device 11. The restoration filler shape determining function 15 determines the shape of the tooth restoration filler 19*a* from the outer shape defined by the outer shape determining function 14 and the bonding shape defined by the bonding shape determining function 13. The electrical circuit 4 has the milling control function 16 which controls the three-dimensional cutter 5 in order to make a tooth restoration filler 19*a* according to an output of the restoration filler shape determining function 15. The tooth restoration filler 19*a* is made of metals, ceramic materials, hard resin and the like as seen in FIG. 7. It is noted that an optical projector may be used when the tooth restoration filler 19*a* is made of the resin. It is also noted that the tooth restoration filler 19*a* is supported inside the pulp root canal 19 by means of an adhesive as shown in FIG. 3.

According to the fifth embodiment of the invention, the preparing probe 31 inside the pulp root canal 19 is measured through the MRI device 2 by making the preparing probe 31 from magnetic material. Thus, the dental pulp 18 can be removed even though it is usually difficult for the MRI device 2 to measure the inside the pulp root canal 19 from which the hard portion 32 and the dental pulp 18 is removed because the inside of the pulp root canal 19 is short of the mobile hydrogen protons. This enables one to precisely remove the dental pulp 18 so as to significantly improve the dental therapeutical technique. Instead of the resin which has been used in the prior art, the inside of the pulp root canal 19 is filled with the hard substance filler. This makes it possible to effectively protect the inside the tooth against the tissue change and the dead voids which otherwise cause inflammation. With the use of the MRI contrast medium 40 and the MRI device 2, the shape of the tooth restoration filler 19*a* is determined on the basis of the inside shape of the pulp root canal 19 so as to make the tooth restoration filler 19*a* by using CAM (computer-aided manufacturer). This enables to precisely and quickly make the tooth restoration filler 19*a*.

As a modification of the fifth embodiment of the invention in which the preparing probe 31 is used to mill the dental pulp of the cure tooth, a rotary type of a preparing probe may be used to cure the tooth. A candid camera, polyp removing tool, curettage, extractor, catheter sonde, or other probe may be used which are respectively inserted in the bone structure, stomach, intestine, nostril, blood vessel, and the like. This is particularly effective in measuring the position of the preparing probe 31 when it is inserted in the living body in which a dilated space is provided by pneumatic means. This is also advantageous when measuring the position of the preparing probe 31 inserted in bone tissue and subnostril which are otherwise difficult to examine by the MRI device 2. It is noted that a magnetism-laden insert probe may be used, and a resin-dispersed insert probe may be employed. It is appreciated that magnetism may be laden on a part of the insert probe to confirm the specified position of the insert probe. It is also appreciated that the MRI contrast medium 40 may be supplied to the dental pulp 18 before removing it to clearly examine the dental pulp 18. It is noted that it is possible to measure the jaw bone in the mouth which is relatively poor in the mobile hydrogen protons instead of the examples in which the shape of the dental root and the dental pulp are measured by means of the MRI contrast medium 40. It is further noted that a fluid contrast medium may be employed to thinly apply it to the article by means of splay coating or brushing when the MRI contrast medium 40 is used as a magnetic material.

Figure 12:
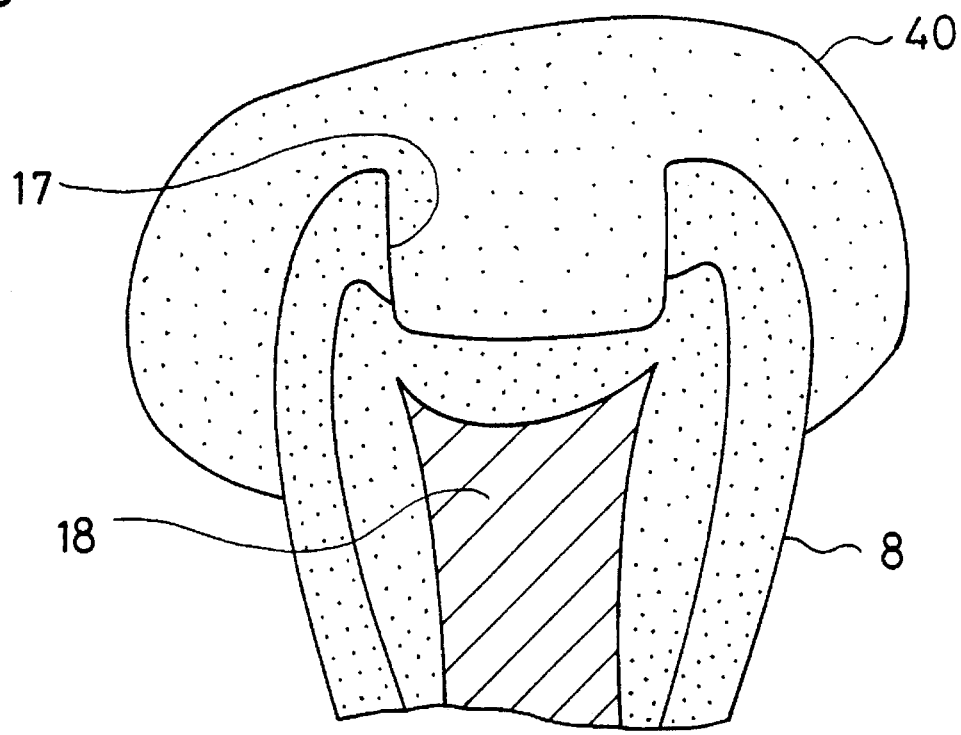
FIG. 12 is a cross sectional view of the tooth in which the MRI contrast filler is supplied according to a sixth embodiment of the invention.

FIG. 12 shows the cure tooth 8 which has a cavity 17 provided at the time of curing the cure tooth 8 according to a sixth embodiment of the invention. In the cavity 17, the MRI contrast medium 40 is supplied to measure the shape of the cavity 17 by the MRI device 2. By using the restoration device 1 of the first embodiment of the invention, the shape of the tooth restoration filler 3 is precisely and quickly provided on the basis of the measured shape of the cavity 17. Further, the distance between an inner wall of cavity 17 and the dental pulp 18 is measured by supplying the MRI contrast medium 40 in the cavity 17 and measuring its shape through the MRI device 2.

Figure 13:
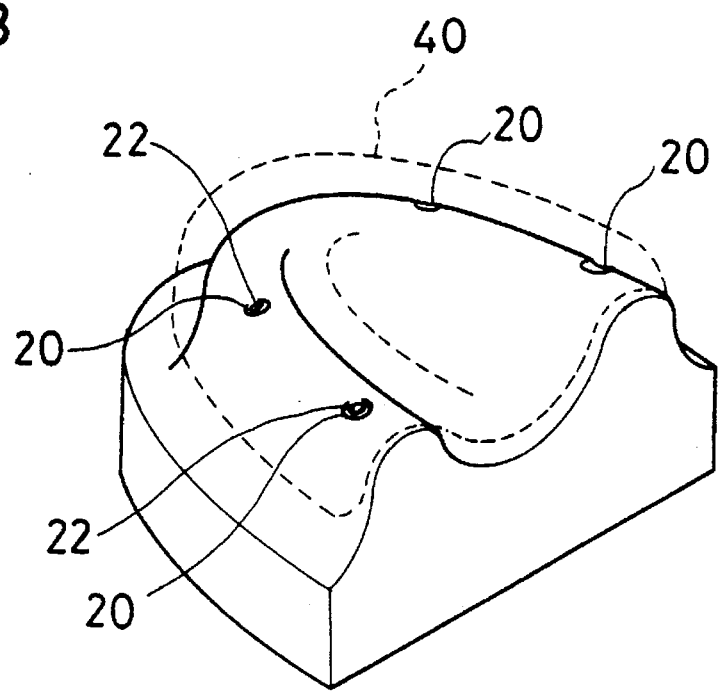
FIG. 13 is a schematic perspective view of the implant structure according to a seventh embodiment of the invention.

FIG. 13 shows the implant structure 20 which serves as an article to be measured according to a seventh embodiment of the invention. The implant structure 20 is supplied by the MRI contrast medium 40. By measuring the implant structure 20 through the MRI contrast medium 40, it is possible to measure the direction and the position of the screw hole 22 through which the prosthesis 21 (FIG. 9) is attached to the implant structure 20. On the basis of the determined position and direction of the screw hole 22, the throughhole 24 is provided with the prosthesis 21 through which the screw 23 passes to attach the prosthesis 21 to the implant structure 20 by using the three-dimensional cutter such as CAM (computer-aided machine).

Figure 14:
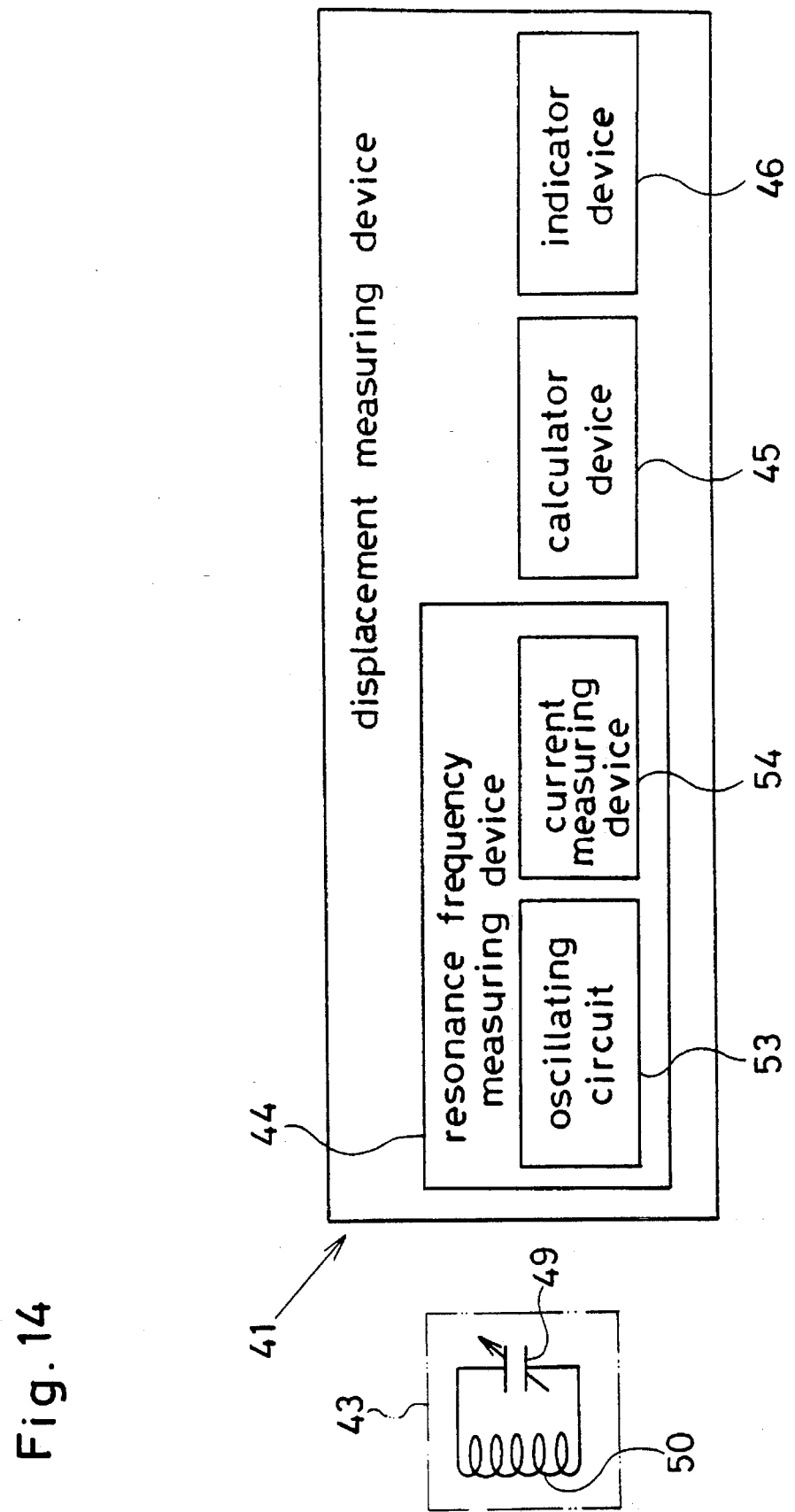
FIG. 14 is a schematic view of a displacement measurement device according to a eight embodiment of the invention.
Figure 15:
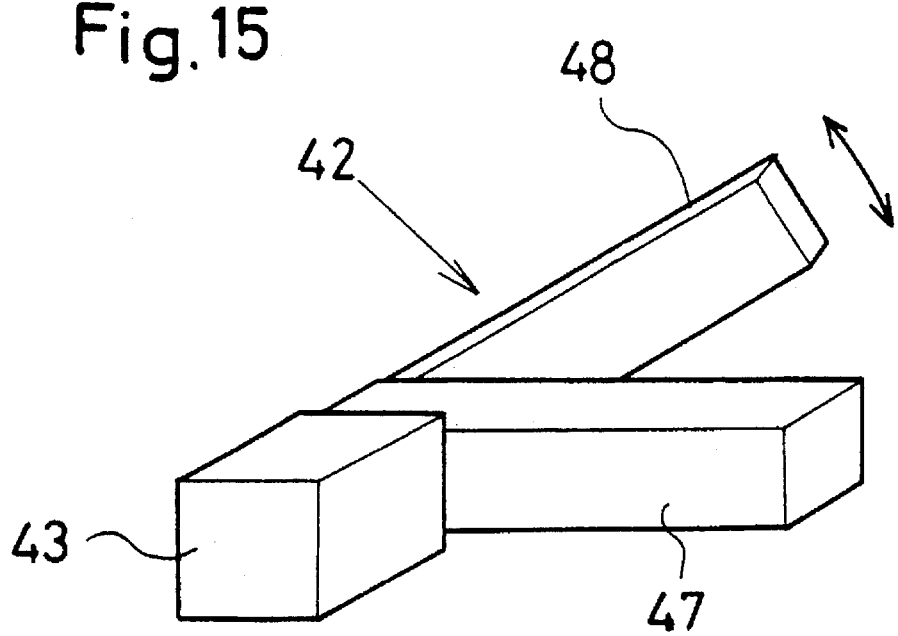
FIG. 15 is a block diagram of the article to be measured according to the eighth embodiment of the invention.

FIG. 14 shows a displacement measuring device 41 according to an eighth embodiment of the invention. The displacement measuring device 41 is provided to detect a rotational angle as one example of a displacement factor. The displacement measuring device 41 has an LC-resonance circuit 43 which is attached to an article 42 (FIG. 15). A resonance frequency measuring device 44 is provided to detect the resonance frequency of the LC-resonance circuit 43. A calculator device 45 is provided to detect the rotational angle of the article 42 on the basis of the detected resonance frequency. An indicator device 46 is provided to display the calculated rotational angle of the article 42. The article 42 serves as a mechanical element in which a second member 48 rotationally moves in relative to a first member 47.

Figure 16:
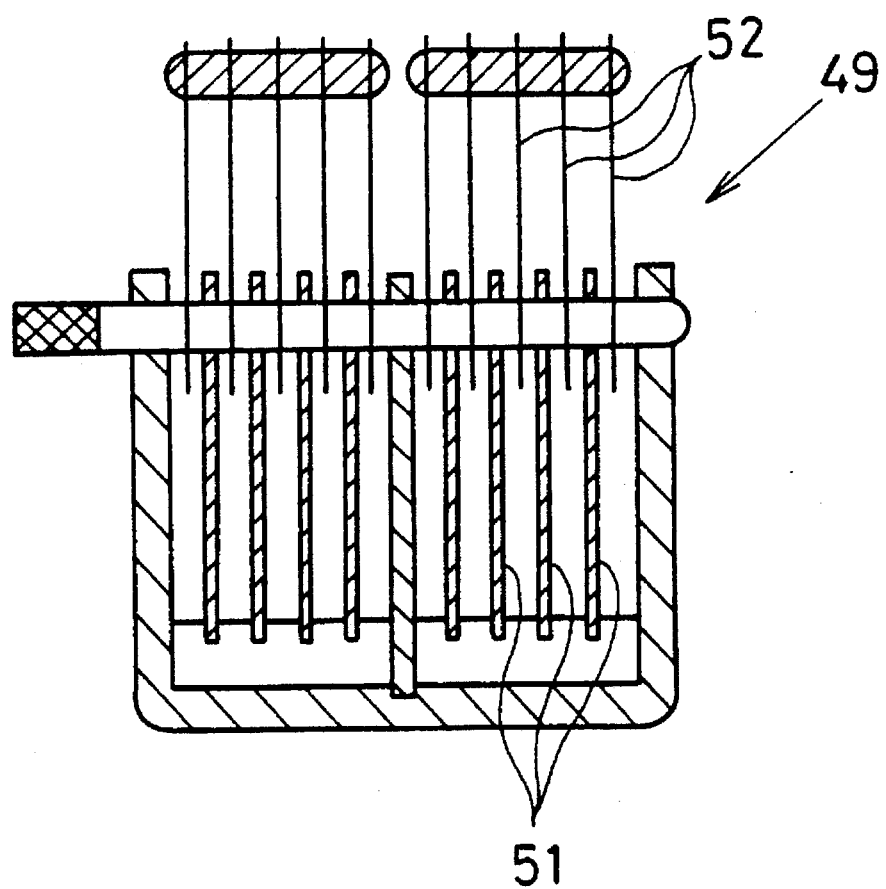
FIG. 16 is a cross sectional view of an air variable capacitor according to the eighth embodiment of the invention.

In the LC-resonance circuit 43, a variable capacitor 49 and a coil 50 are provided in which the capacitor 49 changes its capacitance according to the rotational movement between the second member 48 and the first member 47. The LC-resonance circuit 43 changes its resonance frequency according to the angular movement between the second member 48 and the first member 47. The variable capacitor 49 is in the form of an air variable capacitor and has a plurality of stationary electrodes 51 connected to the first member 47 and a plurality of movable electrodes 52 connected to the second member 48 as shown in FIG. 16. The overlapping area between the stationary electrodes 51 and the movable electrodes 52 changes to vary the capacitance according to the angular movement between the second member 48 and the first member 47. It is noted that the various types of the variable capacitors are introduced as follows:

(1) A linear capacity type which linearly changes the capacity according to the rotational angle.

(2) A liner wave type which changes its resonance wave according to the rotational angle.

(3) A linear frequency type which changes its resonance frequency according to the rotational angle.

(4) An exponential type which changes its capacity, wave or frequency according to the rotational angle.

Among these various types, one can be readily used when the LC-resonance circuit 43 linearly changes its resonance frequency according to the rotational angle. It is noted that the coil 50 may be selected among air core type or magnetic core type coils. The coil 50 may be a variable coil which changes its inductance.

When the variable coil is selected, the coil acts not to change its inductance according to the rotational angle, but works to change the resonance zone of the resonance frequency. This type of coil can eliminate the overlap of the resonance frequency among each of the LC-resonance circuits 43 when detecting angles of a plurality of the articles 42. When a stationary type of coil is used as the coil 50, it is possible to change the resonance zone of the resonance frequency by adding a capacitor and a coil to the LC-resonance circuit 43.

On the other hand, the resonance frequency measuring device 44 is adapted to measure the resonance frequency of the LC-resonance circuit 43 by using a non-contact technique of a dip meter, for example. The dip meter has an oscillating circuit 53 which transmits a consecutively changing oscillating frequency. A current measuring device 54 is provided to measure the intensity of current which is used to oscillate the oscillating circuit 53. In the dip meter, the oscillating frequency of the oscillating circuit 53 is consecutively changed within the resonance frequency zone of the LC-resonance circuit 43. When the oscillating frequency of the oscillating circuit 53 corresponds to the resonance frequency of the LC-resonance circuit 43, the current measured by the current measuring device 54 drops due to the resonance phenomenon. That is to say, the oscillating frequency in which the current drops serves as the oscillating frequency of the LC-resonance circuit 43.

In the calculator device 45, the rotational angle of the article 42 is measured on the basis of the resonance frequency since the resonance frequency of the LC-resonance circuit 43 corresponds to the rotational angle of the article 42. In this instance, the rotational angle of the article 42 is measured on the basis of the rotational angle and the resonance frequency previously determined by experimental test results. The rotational angle of the article 42 determined by the calculator device 45 is displayed via the indicator device 46. When the rotational angle of the article 42 changes constantly, the rotational angle is read by controlling the dip meter through a computer. This holds true when the rotational angle of the article 42 changes rapidly, and a plurality of rotational angles are detected concurrently. That is to say, the sweep speed of the oscillating circuit 53 is controlled by the computer, and at the same time, the current change of the current measuring device 54 is read every sweep by the computer. In this instance, the sweep speed signifies to consecutively change the oscillating frequency. On the basis of the oscillating frequency in which the current drops, the resonance frequency of the LC-resonance circuit 43 is measured to determine the rotational angle of the article 42. It is noted that the rotational angle of the article 42 measured by the computer may be used as an input signal for various types of controller devices. When the rotational angle of the article 42 is used as the input signal, the resonance frequency may be employed as the rotational angle of the article 42.

With the structure thus described, the capacitance of the variable capacitor 49 of the LC-resonance circuit 43 changes when the second member 48 rotates relative to the first member 47. The changed capacitance varies the resonance frequency of the LC-resonance circuit 43. The article 42 continuously changes the resonance frequency within the resonance frequency zone of the LC-resonance circuit 43 due to the oscillating circuit 53. When the oscillating frequency of the oscillating circuit 53 corresponds to the resonance frequency of the LC-resonance circuit 43, the current measured by the current measuring device 54 drops due to the resonance phenomenon. On the basis of the dropped current, the rotational angle of the article 42 is calculated by the calculator device 45. The calculated angle is displayed on the indicator device 46.

According to the eighth embodiment of the invention, the rotational angle of the article 42 is measured by non-contact technique. The LC-resonance circuit 43 consists of only the variable capacitor 49 and the coil 50 so that the whole structure of the LC-resonance circuit 43 is small scale and light weight and simple in structure. That is to say, the LC-resonance circuit 43 is space-saving, cost-saving and helps to lighten the burden of the article 42 when it is attached to the article 42.

Figure 17:
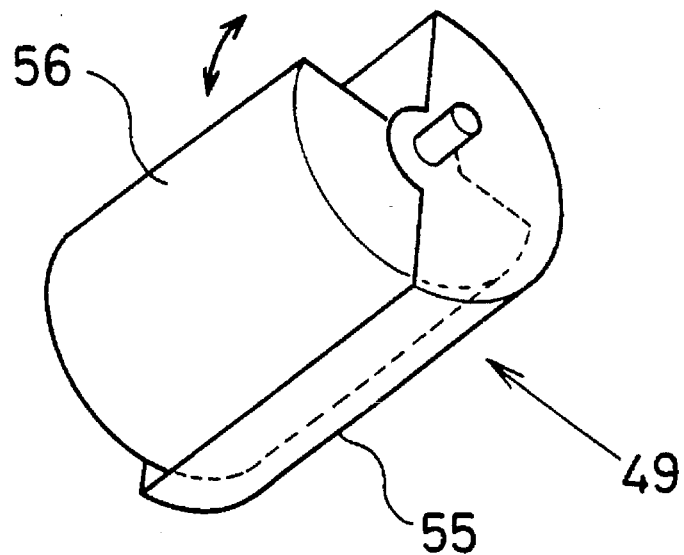
FIG. 17 is a perspective view of an air variable capacitor according to a ninth embodiment of the invention.

FIG. 17 shows the variable capacitor 49 according to a ninth embodiment of the invention. The variable capacitor 49 serves as a cylinder type of air variable capacitor, and having an outer cylinder 55 connected to the first member 47 and an inner cylinder 56 connected to the second member 48. The overlapping area of the outer cylinder 55 and the inner cylinder 56 changes depending on the relative movement of the first member 47 and the second member 48 so as to vary the capacitance.

Figure 18:
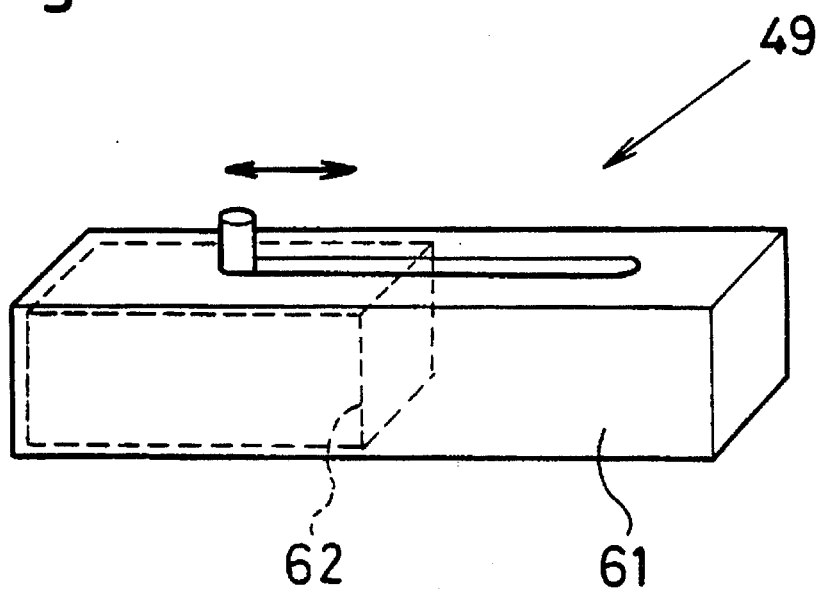
FIG. 18 is a perspective view of an air variable capacitor according to a tenth embodiment of the invention.

FIG. 18 shows the variable capacitor 49 according to a tenth embodiment of the invention. The variable capacitor 49 is in the form of a slider type capacitor which is applied to a displacement detecting device so as to detect the movement of the first member 47 and the second member 48. The variable capacitor 49 has an outer cylinder 61 connected to the first member 47 and an inner cylinder 62 connected to the second member 48. A linear change of the first member 47 and the second member 48 varies an overlapping area between a stationary electrode of the outer cylinder 61 and a movable electrode of the inner cylinder 62 so as to change the capacitance. On the basis of the changed capacitance, the linear change of the first member 47 and the second member 48 is measured in the same manner as described in the ninth embodiment of the invention. It is noted that each of the stationary electrode and the movable electrode may be laminated like multi-layer configuration.

Figure 19:
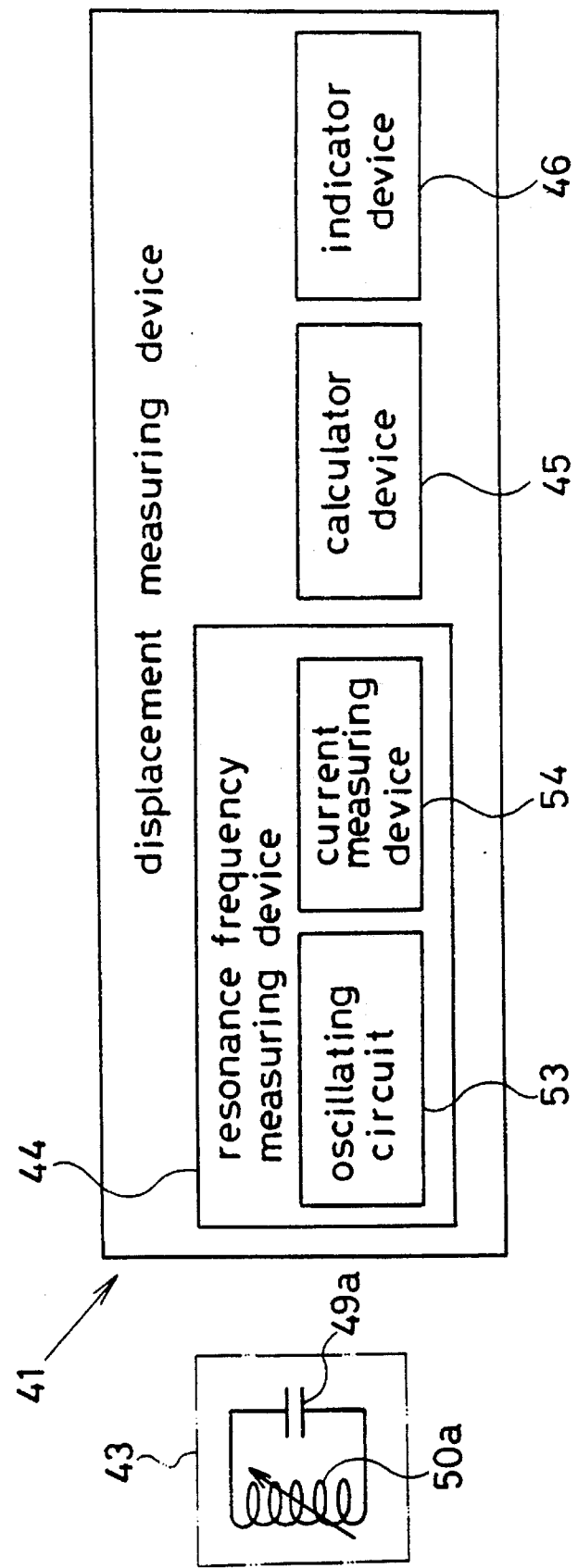
FIG. 19 is a schematic view of a displacement measuring device according to an eleventh embodiment of the invention.
Figure 20:
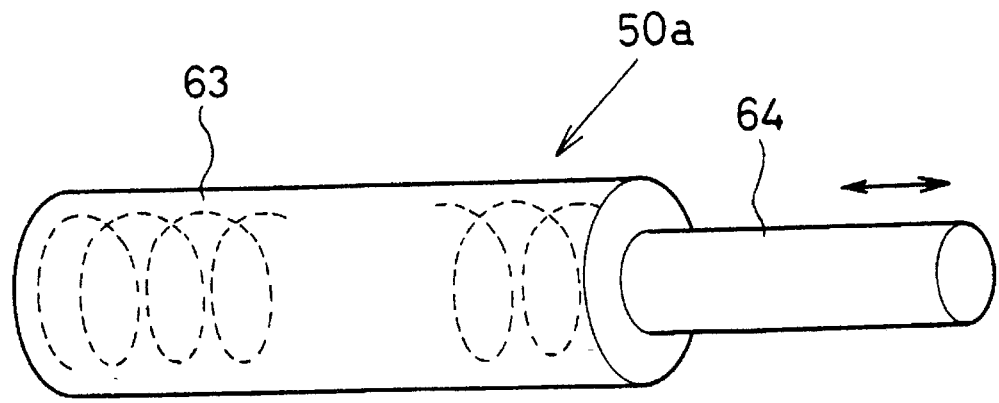
FIG. 20 is a perspective view of a variable coil according to the eleventh embodiment of the invention.

FIG. 19 shows a schematic view of the displacement measuring device 41 according to an eleventh embodiment of the invention. In the LC-resonance circuit 43, in addition to a capacitor 49a, a variable coil 50a is employed to change its inductance depending on the relative movement between the first member 47 and the second member 48. The variable coil 50a works to measure the linear movement of the article, and has a cylinder coil 63 connected to the first member 47 and a magnetic core 64 connected the second member 48 as shown in FIG. 20. The insert amount of the magnetic core 64 to the coil 63 changes to vary its inductance depending on the linear movement of the first member 47 and the second member 48. That is to say, the resonance frequency of the LC-resonance circuit 43 changes depending on the linear movement of the first member 47 and the second member 48. On the basis of the changed resonance frequency, the linear movement of the first member 47 and the second member 48 is measured. It is noted that the capacitor 49a employed herein may be a stationary type and a variable type. When the variable type of capacitor is selected, it is possible to change the resonance frequency zone by predetermining the capacitance of the capacitor arbitrarily.

Figure 21:
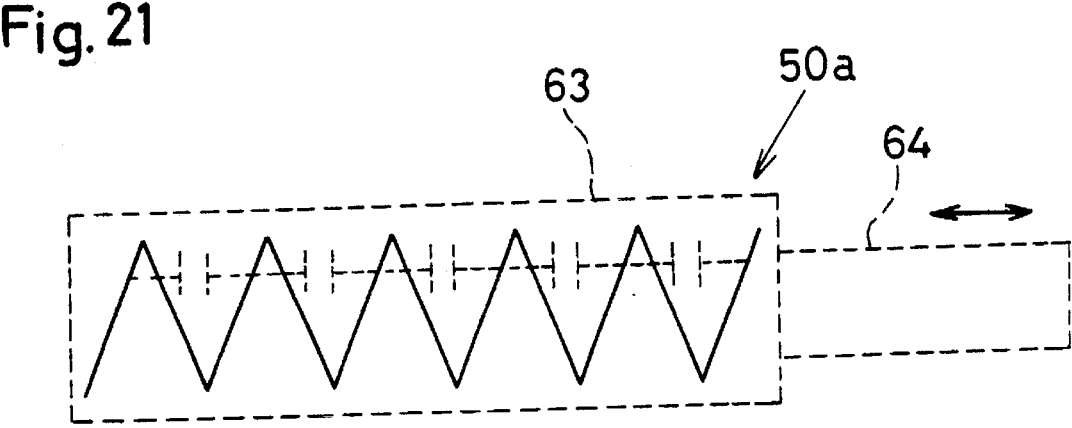
FIG. 21 is a perspective view of a coil according to a twelfth embodiment of the invention.

FIG. 21 shows a schematic view of the variable coil 50a according to a twelfth embodiment of the invention. In a resonance circuit of the twelfth embodiment of the invention, the resonance circuit consists of only the variable coil 50a without using any capacitor as an electronic device. The resonance circuit has the cylinder coil 63 connected to the first member 47 and the magnetic core 64 connected the second member 48 in the same manner as described in the eleventh embodiment of the invention. Although the resonance circuit dispenses without any capacitor according to the eleventh embodiment of the invention, the resonance circuit substantially form an LC-resonance circuit when considering a self-capacitance of the cylinder coil 63.

Figure 22:
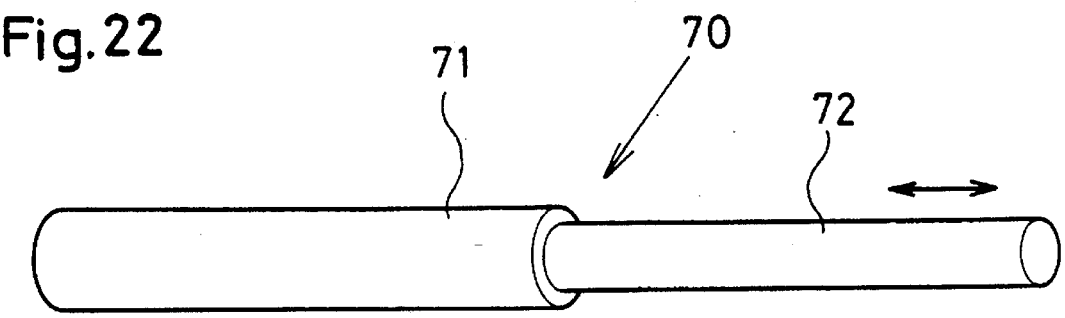
FIG. 22 is a schematic view of an antenna resonance circuit according to a thirteenth embodiment of the invention.

FIG. 22 shows a schematic view of an antenna resonance circuit 70 in which a received frequency changes depending on the movement of the article according to a thirteenth embodiment of the invention. The antenna resonance circuit 70 has a cylinder rod 71 connected to the first member 47 of the article and an elongation rod 72 connected the second member 48. A linear movement of the first member 47 and the second member 48 changes the insert amount of the elongation rod 72 to cylinder rod 71 so as to vary the resonance frequency (received frequency). That is to say, the resonance frequency of the antenna resonance circuit 70 changes depending on the linear movement of the first member 47 and the second member 48. On the basis of the changed resonance frequency, the linear displacement of the first member 47 and the second member 48 is determined.

Figure 23:
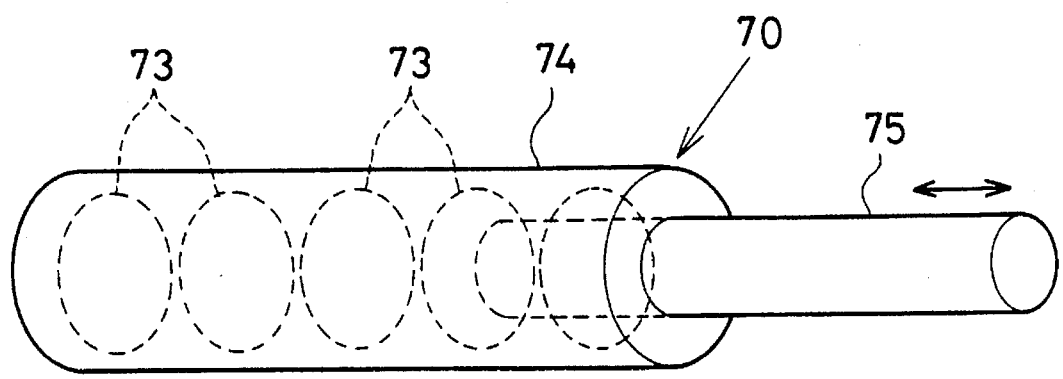
FIG. 23 is a schematic view of an antenna resonance circuit according to a fourteenth embodiment of the invention.

FIG. 23 shows a schematic perspective view of the antenna resonance circuit 70 according to a fourteenth embodiment of the invention. In the antenna resonance circuit 70 according to a fourteenth embodiment of the invention, there is provided a cylindrical body 74 connected to the first member 47. A plurality of looped antennas 73 are disposed in the cylindrical body 74 at regular intervals. An elongated magnetic core 75 is connected to the second member 48, and axially movably disposed in the cylindrical body 74. In the antenna resonance circuit 70, the resonance frequency changes depending on the insert amount of the core 75 to the cylindrical body 74 so as to continuously measure the positional relationship between the first member 47 and the second member 48 even when a leading end of the core 75 is located between the neighboring looped antennas 73.

Figure 24:
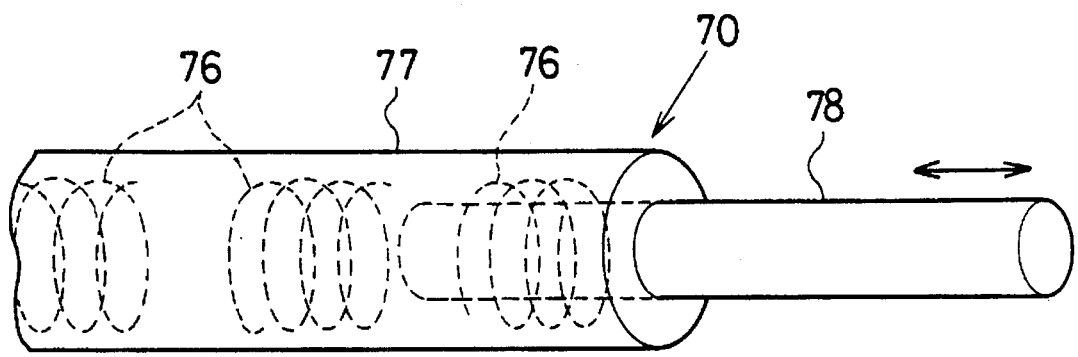
FIG. 24 is a schematic view of an antenna resonance circuit according to a fifteenth embodiment of the invention.

FIG. 24 shows a schematic perspective view of an antenna resonance circuit 70 according to a fifteenth embodiment of the invention. In the antenna resonance circuit 70 according to a fifteenth embodiment of the invention, there is provided a cylindrical body 77 connected to the first member 47. A plurality of coiled antennas 76 are disposed in the cylindrical body 77 at regular intervals. An elongated magnetic core 78 is connected to the second member 48, and axially movably disposed in the cylindrical body 77.

It is observed that any type of an air variable capacitor may be used except for ones employed in the eighth~fifteenth embodiments of the invention. A magnetically variable capacitor, poly variable capacitor, trimer capacitor may be used as alternative variable capacitors.

In the eleventh and twelfth embodiments of the invention, the linear movement is measured by changing the inductance depending on the displacement of the article, and it is possible to measure the rotational angle by changing the capacitance depending on the rotational movement of the article.

It is also observed that a resistor may be added to the LC-resonance circuit in the eighth~twelfth embodiments of the invention.

In the thirteenth~fifteenth embodiments of the invention, the received frequency is changed according to the linear movement of the article so as to measure the linear displacement. It is appreciated that it is possible to change the received frequency depending on the rotational movement of the article so as to measure the rotational angle. It is also possible to treat the resonance frequency as a displacement of the article since the resonance frequency corresponds to the displacement of the article.

In the above embodiments of the invention, the resonance frequency is measured by supplying voltage to the oscillating circuit. It is possible to generate pulse signals (in the form of rectangular wave) at the resonance frequency measurement device. This makes it possible to measure a length of echo due to the resonance of the resonance circuit. In this instance, it is also possible to adopt the echo-back method in which an intensity of the echo is measured to detect the resonance frequency. It is noted that a high frequency bridge measurement method may be adopted.

It is further noted that it is possible to transmit the resonance frequency from the resonance circuit so that the resonance frequency measuring device receives the resonance frequency.

The resonance circuit is made from the electronic device in the above embodiments of the invention, the resonance circuit may be made from molecular level and crystallization body. In this instance, L, LC and LCR resonance circuit may be made of the molecular level and the crystallization body, or otherwise the circuit may be made of an equivalent circuit. These types of the circuits are well-suited for sensors of micromachines.

While the invention has been described with reference to the specific embodiments, it is understood that this description is not to be construed in a limiting sense in as much as various modifications and additions to the specific embodiments may be made by skilled artisan without departing from the spirit and scope of the invention.

What is claimed is:

1. A method of determining a shape of an article based on resonant properties of an MRI contrast medium, comprising the steps of:

providing said article, wherein said article is one of teeth, a prosthesis, a jaw bone, and an implant structure and wherein said article lacks or is short of hydrogen protons;

providing said MRI contrast medium which is rich in hydrogen proton;

supplying said article with said MRI contrast medium, wherein said MRI contrast medium is in a liquid state at least when said MRI contrast medium is supplied to said article;

measuring said MRI contrast medium with an MRI device; and determining said shape of said article on the basis of a configuration of said MRI contrast medium.

2. The method as recited in claim 1, further comprising the steps of:

providing a measurement cover for at least partially surrounding said article;

retaining said MRI contrast medium around at least part of said article by said measurement cover.

3. The method as recited in claims 1 or 2 wherein said article is a cure tooth, and wherein said method further comprises the step of:

curing said cure tooth.

4. The method as recited in claims 1 or 2 wherein said article is a cure tooth and wherein said method, further comprises the step of:

determining a distance between dental pulp of said cure tooth and another portion of said cure tooth based on said measurement of said MRI contrast medium by said MRI device.

5. The method as recited in claims 1 or 2, wherein said article is one of an upper tooth and a lower tooth disposed below said upper tooth, wherein said MRI contrast medium is located between said upper tooth and said lower tooth, and wherein said MRI contrast medium is measured by said MRI device so as to determine a central occlusive position and an eccentric occlusive position of said upper tooth and said lower tooth.

6. The method as recited in claims 1 or 2 wherein said article is said implant structure and wherein said method comprises the steps of:

attaching said implant structure to a jaw bone; and determining a position at which a prosthesis is to be bonded to said implant structure based on said measurement of said MRI contrast medium by said MRI device.

7. The method according to claim 1, wherein said MRI contrast medium further provided in said step of providing said MRI contrast medium further comprises magnetic material.

8. A method of forming a tooth restoration filler, comprising the steps of:

supplying a tooth with an MRI contrast medium which is rich in hydrogen protons;

measuring said MRI contrast medium with an MRI device;

determining a shape of said tooth restoration filler by determining a shape of said tooth on the basis of said measurement of said MRI contrast medium; and manufacturing said tooth restoration filler with a three-dimensional cutter on the basis of said shape of said tooth restoration filler.

9. The method according to claim 8, wherein said MRI contrast medium provided in said step of supplying said tooth with said MRI contrast medium further comprises magnetic material.

10. An apparatus for making a tooth crowning filler comprising:

an MRI contrast medium;

an MRI means for measuring a cure tooth supplied with said MRI contrast medium, wherein said MRI contrast medium is rich in hydrogen protons;

an electrical circuit means for determining a shape of said cure tooth on the basis of a measurement of said MRI contrast medium measured by said MRI means;

a three-dimensional cutter means for forming a tooth crowning filler on the basis of said shape of said cure tooth determined by said MRI means.

11. The apparatus according to claim 10, wherein said MRI contrast medium comprises magnetic material.

12. A method of determining a shape of an article based on resonant properties of an MRI contrast medium, comprising the steps of:

providing said article, wherein said article is one of teeth, a prosthesis, a jaw bone, and an implant structure and wherein said article lacks or is short of hydrogen protons;

providing said MRI contrast medium which is rich in magnetic material;

coating said article with said MRI contrast medium, wherein said MRI contrast medium is in a liquid state at least when said article is coated with said MRI contrast medium;

measuring said MRI contrast medium with an MRI device; and determining said shape of said article on the basis of a configuration of said MRI contrast medium.

13. The method as recited in claim 12, further comprising the steps of:

providing a measurement cover for at least partially surrounding said article;

retaining said MRI contrast medium around at least part of said article by said measurement cover.

14. The method as recited in claim 12 wherein said article is said implant structure and wherein said method comprises the steps of:

attaching said implant structure to a jaw bone; and determining a position at which a prosthesis is to be bonded to said implant structure based on said measurement of said MRI contrast medium by said MRI device.

15. The method as recited in claim 12 wherein said article is a a cure tooth having a dental root canal, wherein dental pulp is removed from said dental root canal, and wherein said method further comprises the step of:

determining a shape of said dental root canal based on said measurement of said MRI contrast medium by said MRI device.

16. The method according to claim 12, wherein said MRI contrast medium provided in said step of providing said MRI contrast medium further comprises hydrogen protons.

* * * * *